(12) United States Patent
Nakamura et al.

(10) Patent No.: US 10,487,030 B2
(45) Date of Patent: *Nov. 26, 2019

(54) SOLVENT COMPOSITION, CLEANING METHOD, METHOD OF FORMING A COATING FILM, HEAT TRANSFER FLUID, AND HEAT CYCLE SYSTEM

(71) Applicant: AGC Inc., Chiyoda-ku (JP)

(72) Inventors: Masahiko Nakamura, Chiyoda-ku (JP); Hiroaki Mitsuoka, Chiyoda-ku (JP); Mari Ichinokawa, Chiyoda-ku (JP); Atsushi Fujimori, Chiyoda-ku (JP); Hidekazu Okamoto, Chiyoda-ku (JP)

(73) Assignee: AGC Inc., Chiyoda-ku (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/865,493

(22) Filed: Jan. 9, 2018

(65) Prior Publication Data

US 2018/0127341 A1    May 10, 2018

Related U.S. Application Data

(63) Continuation of application No. PCT/JP2016/062476, filed on Apr. 20, 2016.

(30) Foreign Application Priority Data

Jul. 27, 2015  (JP) .................................. 2015-148070
Jan. 15, 2016  (JP) .................................. 2016-005952

(51) Int. Cl.
| | | |
|---|---|---|
| C07C 21/18 | (2006.01) | |
| C09D 201/00 | (2006.01) | |
| C09D 7/20 | (2018.01) | |
| C07C 21/22 | (2006.01) | |
| C09K 5/10 | (2006.01) | |
| C11D 3/43 | (2006.01) | |
| C07C 19/10 | (2006.01) | |
| C09K 5/04 | (2006.01) | |
| C11D 7/50 | (2006.01) | |
| C11D 11/00 | (2006.01) | |
| C08K 5/02 | (2006.01) | |

(52) U.S. Cl.
CPC .............. *C07C 21/18* (2013.01); *C07C 19/10* (2013.01); *C07C 21/22* (2013.01); *C09D 7/20* (2018.01); *C09D 201/00* (2013.01); *C09K 5/044* (2013.01); *C09K 5/10* (2013.01); *C11D 3/43* (2013.01); *C11D 7/5018* (2013.01); *C11D 11/0017* (2013.01); *C08K 5/02* (2013.01); *C09K 2205/126* (2013.01)

(58) Field of Classification Search
CPC ......... C07C 21/18; C07C 19/10; C07C 21/22; C11D 3/43; C11D 3/24; C09K 5/10; C09K 5/04; C09D 7/20; C09D 7/40; C09D 201/00

USPC ..................................................... 252/67, 364
See application file for complete search history.

(56) References Cited

U.S. PATENT DOCUMENTS

| | | | | |
|---|---|---|---|---|
| 5,629,461 | A * | 5/1997 | Yasuhara | .............. C07C 17/206 |
| | | | | 570/166 |
| 10,029,961 | B2 * | 7/2018 | Deur-Bert | ............. C07C 17/383 |
| 10,221,112 | B2 * | 3/2019 | Ichinokawa | ............. C07C 21/18 |
| 2012/0161063 | A1 * | 6/2012 | Singh | ........................ C08J 9/144 |
| | | | | 252/67 |
| 2013/0105724 | A1 | 5/2013 | Boussand | |
| 2018/0127341 | A1 * | 5/2018 | Nakamura | ............... C09K 5/04 |
| 2018/0134640 | A1 * | 5/2018 | Nakamura | ............... C09K 5/04 |
| 2018/0162794 | A1 * | 6/2018 | Ichinokawa | ............. C07C 17/25 |
| 2018/0319726 | A1 * | 11/2018 | Mitsuoka | ................. B05D 7/00 |

FOREIGN PATENT DOCUMENTS

| | | |
|---|---|---|
| CN | 102596869 A | 7/2012 |
| CN | 102985397 A | 3/2013 |
| EP | 3 330 243 A1 | 6/2018 |
| EP | 3 330 346 A1 | 6/2018 |

(Continued)

OTHER PUBLICATIONS

International Search Report dated Jun. 7, 2016 in PCT/JP2016/062476, filed on Apr. 20, 2016 (with English Translation).

(Continued)

*Primary Examiner* — Douglas J Mc Ginty
(74) *Attorney, Agent, or Firm* — Oblon, McClelland, Maier & Neustadt, L.L.P.

(57) ABSTRACT

There are provided: a solvent composition which is excellent in solubility of various organic substances and excellent in detergency, and has no adverse effect on a global environment, is excellent in stability, and is capable of suppressing corrosion of metal; a cleaning method using the solvent composition; a method of forming a coating film; a heat transfer fluid including the solvent composition; and a heat cycle system using the heat transfer fluid. A solvent composition including HCFO-1233yd and HCFC-244ca, in which a content of HCFC-244ca to a total of HCFO-1233yd and HCFC-244ca is 0.0001 to 1 mass %, a cleaning method of contacting the solvent composition with an article, a method of forming a coating film consisting of the nonvolatile organic compound using the solvent composition and a nonvolatile organic compound, a heat transfer fluid including the solvent composition, and a heat cycle system using the heat transfer fluid.

16 Claims, 1 Drawing Sheet

(56) References Cited

FOREIGN PATENT DOCUMENTS

| FR | 2 962 442 A1 | 1/2012 |
|---|---|---|
| FR | 3 015 478 B1 | 6/2015 |
| JP | 2-204424 | 8/1990 |
| JP | 5-339181 | 12/1993 |
| JP | 2013-504658 | 2/2013 |
| JP | 2013-506731 | 2/2013 |
| JP | 2013-544896 | 12/2013 |
| WO | WO 94/14737 A1 | 7/1994 |
| WO | WO 2008/149907 A1 | 12/2008 |
| WO | WO 2011/031697 A2 | 3/2011 |
| WO | WO 2011/041286 A2 | 4/2011 |
| WO | WO 2012/004487 A2 | 1/2012 |
| WO | WO 2015/092211 A1 | 6/2015 |
| WO | WO-2018139653 A1 * | 8/2018 |

OTHER PUBLICATIONS

Written Opinion dated Jun. 7, 2016 in PCT/JP2016/062476, filed on Apr. 20, 2016.

* cited by examiner

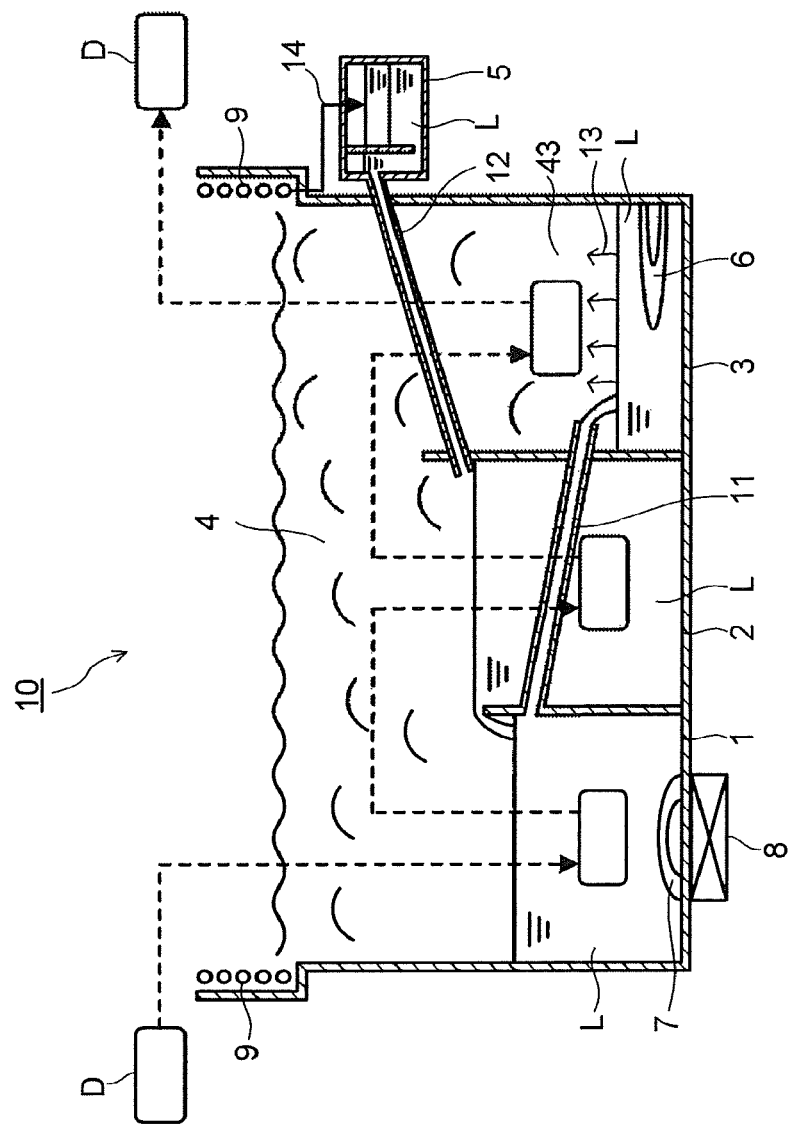

SOLVENT COMPOSITION, CLEANING METHOD, METHOD OF FORMING A COATING FILM, HEAT TRANSFER FLUID, AND HEAT CYCLE SYSTEM

CROSS-REFERENCE TO RELATED APPLICATIONS

This application is a continuation of prior International Application No. PCT/JP2016/062476, filed on Apr. 20, 2016 which is based upon and claims the benefit of priority from Japanese Patent Applications No. 2015-148070, filed on Jul. 27, 2015 and No. 2016-005952, filed on Jan. 15, 2016; the entire contents of all of which are incorporated herein by reference.

FIELD

The present invention relates to a solvent composition which is excellent in solubility of various organic substances and excellent in detergency, and has no adverse effect on a global environment, is excellent in stability, and is capable of suppressing corrosion of metal. Specifically, the solvent composition of the present invention can be used in a wide range of uses, such as a cleaning solvent, a dilution coating solvent, and a heat transfer fluid.

BACKGROUND

In manufacture of IC, an electronic component, a precision machinery component, an optical component, and the like, in a manufacturing process, an assembly process, a final finishing process, and the like, components are cleaned by a cleaning solvent, thereby removing flux, a processing oil, wax, a release agent, dust, and the like adhering to the components. Further, as a method of manufacturing an article having a coating film containing various organic chemical substances such as a lubricant, for example, there is known a method in which a solution in which the organic chemical substances have been dissolved in a dilution coating solvent is prepared, the solution is applied on an article to be coated, and thereafter the dilution coating solvent is evaporated to form a coating film. The dilution coating solvent is required to allow the organic chemical substances to be dissolved sufficiently and to have a sufficient drying property as well.

As a solvent to be used in such uses, in that it has incombustibility and low toxicity, is excellent in stability, does not encroach on a base material of metal, plastic, elastomer, or the like, and is excellent in chemical and thermal stability, there has been used a fluorinated solvent or the like containing a chlorofluorocarbon (hereinafter, mentioned as "CFC") such as 1,1,2-trichloro-1,2,2-trifluoroethane, a hydrochlorofluorocarbon (hereinafter, mentioned as "HCFC") such as 2,2-dichloro-1,1,1-trifluoroethane, 1,1-dichloro-1-fluoroethane, 3,3-dichloro-1,1,1,2,2-pentafluoropropane, and 1,3-dichloro-1,1,2,2,3-pentafluoropropane, or the like.

However, because the CFCs and the HCFCs are chemically very stable, they each have a long lifetime in the troposphere after vaporization, and diffuse and reach the stratosphere. Therefore, there is a problem that the CFCs and the HCFCs which have reached the stratosphere are decomposed by ultraviolet rays and generate chlorine radicals to deplete an ozone layer.

On the other hand, as a solvent having no chlorine atom and having no adverse effect on the ozone layer, a perfluorocarbon (hereinafter, mentioned as "PFC") is known. In addition, as an alternative solvent to the CFCs and the HCFCs, a hydrofluorocarbon (hereinafter, mentioned as "HFC"), a hydrofluoroether (hereinafter, mentioned as "HFE"), and the like are also under development. However, because the HFCs and the PFCs have a high global warming potential, they are substances subject to regulation by the Kyoto Protocol.

As a new solvent substituted for the solvents of the HFCs, the HFEs, and the PFCs, a fluoroolefin having a double bond between carbon atoms is proposed. Because the fluoroolefin has a short lifetime in the atmosphere due to easy decomposition and its ozone depletion potential and global warming potential are low, it has an excellent property in which an effect on a global environment is small, but on the other hand, it is poor in stability due to the easy decomposition, and there has been a problem that in a case of use as the cleaning solvent or the dilution coating solvent, it decomposes and acidifies in use.

Therefore, in Patent References 1 (JP-A No. 2013-504658) and 2 (JP-A No. 2013-506731), there is disclosed a technology of adding additional components as a lubricant, a stabilizer, a metal passivator, a corrosion inhibitor, a flame inhibitor, and other compound and/or component for regulating a specific property of a composition to a wide variety of fluoroolefins which each include 1-chloro-2,3,3-trifluoro-1-propene and each have a double bond between carbon atoms.

Further, a example in Patent Reference 3 (International Publication WO1994/14737) mentions that by making hydrogen fluoride react with 1-chloro-2,2,3,3-tetrafluoropropane in a gas phase, a slight amount of 1-chloro-2,3,3-trifluoro-1-propene is by-produced together with 1,1,2,2,3-pentafluoropropane.

However, Patent References 1 to 3 do not mention a technology of stabilizing 1-chloro-2,3,3-trifluoro-1-propene by adding a slight amount of 1-chloro-2,2,3,3-tetrafluoropropane to 1-chloro-2,3,3-trifluoro-1-propene.

SUMMARY

In the present invention, it is an article thereof to provide: a solvent composition which is excellent in solubility of various organic substances and excellent in detergency, and has no adverse effect on a global environment, is excellent in stability, and is capable of suppressing corrosion of metal; a cleaning method using the solvent composition; a method of forming a coating film using the solvent composition; a heat transfer fluid including the solvent composition; and a heat cycle system using the heat transfer fluid.

The present inventors have performed studies in consideration of the above-described points, resulting in completing the present invention. That is, the present invention consists the following.

[1] A solvent composition including 1-chloro-2,3,3-trifluoro-1-propene and 1-chloro-2,2,3,3-tetrafluoropropane, in which a proportion of a content of 1-chloro-2,2,3,3-tetrafluoropropane to a total of a content of 1-chloro-2,3,3-trifluoro-1-propene and a content of 1-chloro-2,2,3,3-tetrafluoropropane is 0.0001 to 1 mass %.

[2] The solvent composition according to [1], wherein a proportion of a content of 1-chloro-2,3,3-trifluoro-1-propene to a total amount of the solvent composition is 80 mass % or more.

[3] The solvent composition according to [1], wherein the 1-chloro-2,3,3-trifluoro-1-propene consists of (Z)-1-chloro-2,3,3-trifluoro-1-propene and (E)-1-chloro-2,3,3-trifluoro-1-propene, and a proportion of a content of (Z)-1-chloro-2,3,3-trifluoro-1-propene to a total amount of 1-chloro-2,3,3-trifluoro-1-propene is 80 to 100 mass %.

[4] A cleaning method including bringing the solvent composition according to [1] and an article to be cleaned into contact with each other.

[5] The cleaning method according to [4], wherein a processing oil adhering to the article to be cleaned is cleaned.

[6] The cleaning method according to [5], wherein the processing oil is at least one selected from a group consisting of a cutting oil, a quenching oil, a rolling oil, a lubricating oil, a machine oil, a presswork oil, a stamping oil, a drawing oil, an assembly oil, and a wire drawing oil.

[7] The cleaning method according to [4], wherein the article to be cleaned is clothing.

[8] A method of forming a coating film including dissolving a nonvolatile organic compound in the solvent composition according to [1] to prepare a coating film-forming composition and evaporating the solvent composition after applying the coating film-forming composition on an article to be coated, to form a coating film consisting of the nonvolatile organic compound.

[9] A heat transfer fluid including the solvent composition according to [1].

[10] A heat cycle system using the heat transfer fluid according to [9].

A solvent composition of the present invention is excellent in solubility of various organic substances and excellent in detergency, and has no adverse effect on a global environment, is excellent in stability, and is capable of suppressing corrosion of metal. A cleaning method of the present invention has no adverse effect on a global environment and is excellent in detergency. A method of forming a coating film of the present invention has no adverse effect on a global environment and allows a uniform coating film to be formed. A heat transfer fluid including the solvent composition of the present invention has no adverse effect on a global environment and is excellent in stability. A heat cycle system using the heat transfer fluid of the present invention has no adverse effect on a global environment.

BRIEF DESCRIPTION OF THE DRAWINGS

FIG. 1 is a view schematically illustrating one example of a cleaning apparatus carrying out a cleaning method of the present invention.

MODE FOR CARRYING OUT THE INVENTION

<Solvent Composition>

A solvent composition of the present invention is a solvent composition including 1-chloro-2,3,3-trifluoro-1-propene ($CHCl=CF-CHF_2$, hereinafter mentioned as "HCFO-1233yd") and 1-chloro-2,2,3,3-tetrafluoropropane ($CHF_2-CF_2-CH_2Cl$, hereinafter mentioned as "HCFC-244ca"), and a proportion of a content of HCFC-244ca to a total of a content of HCFO-1233yd and a content of HCFC-244ca is 0.0001 to 1 mass %.

In the solvent composition of the present invention, HCFO-1233yd is a component having an excellent property described below as a solvent, and HCFC-244ca is a component included in the solvent composition as a stabilizer stabilizing HCFO-1233yd.

(HCFO-1233yd)

Because HCFO-1233yd is fluoroolefin having a double bond between carbon atoms, its lifetime in the atmosphere is short and its ozone depletion potential and global warming potential are low.

In HCFC-1233yd, a Z-isomer and an E-isomer which are a geometric isomer exist according to positions of substituents on the double bond. When the compound name or an abbreviated name of the compound is used unless otherwise stated in this description, at least one selected from the Z-isomer and the E-isomer is indicated, and when (E) or (Z) is denoted behind the compound name or the abbreviated name of the compound, an (E)-isomer or a (Z)-isomer of each compound is indicated. For example, HCFO-1223yd (Z) indicates the Z-isomer, and HCFO-1233yd(E) indicates the E-isomer.

A boiling point of HCFO-1233yd(Z) is about 54° C., a boiling point of HCFO-1233yd(E) is about 48° C., and both are substances excellent in a drying property. Further, even though they are boiled to turn into vapor, even parts susceptible to heat, such as resin parts, are not easily adversely affected since the boiling point of HCFO-1233yd(Z) is about 54° C. and the boiling point of HCFO-1233yd(E) is about 48° C. In addition, HCFO-1233yd has excellent ability as a cleaning solvent or a coating solvent, such as no flash point, low surface tension and viscosity, and easy evaporation even at a normal temperature.

Note that in this description, the boiling points of the compounds are boiling points at a normal pressure unless otherwise stated. In this description, the normal pressure means 760 mmHg and the normal temperature means 25° C., respectively.

On the other hand, HCFO-1233yd does not have sufficient stability and when HCFO-1233yd is retained at the normal temperature and the normal pressure, it decomposes in several days to generate chlorine ions. Therefore, in the solvent composition of the present invention, stabilization of HCFO-1233yd is achieved by containing the above-described predetermined amount of HCFC-244ca with HCFO-1233yd.

A proportion of the content of HCFO-1233yd in the solvent composition of the present invention is preferably 50 mass % or more, more preferably 80 mass % or more and furthermore preferably 90 mass % or more to a total amount of the solvent composition. As long as the proportion is equal to or more than the above-described lower limit value, the solvent composition is excellent in solubility of various organic substances and excellent in detergency. The content of HCFO-1233yd is particularly preferably a total amount in which HCFC-244ca has been removed from the solvent composition. That is, the solvent composition particularly preferably consists of only HCFO-1233yd and HCFC-244ca. However, the solvent composition may contain a component which is produced in a manufacturing process of HCFO-1233yd and is difficult to separate from HCFO-1233yd and/or a component which is produced in a manufacturing process of HCFC-244ca and is difficult to separate from HCFC-244ca in a range in which an effect of the present invention is not impaired, for example, by an amount which is 10 mass % or less and preferably 5 mass % or less with respect to the total amount of the solvent composition.

Here, a boiling point of HCFC-244ca is about 53° C. In the solvent composition of the present invention, in the Z-isomer and the E-isomer of HCFO-1233yd, HCFO-1233yd(Z) is preferable to HCFO-1233yd(E) since it is close to HCFC-244ca in the boiling point. As long as a composition of compounds whose boiling points are close to each other is used, even in such use as is accompanied by a phase change between a liquid phase and a gas phased, a composition change does not easily occur between the liquid phase and the gas phase. For example, the solvent composition consisting of HCFO-1233yd(Z) and HCFC-244ca is capable of treating an article to be cleaned in the same composition for a long period due to almost no composition change between the liquid phase and the gas phase in the later-described cleaning method having a solvent contact step in which the article to be cleaned is brought into contact with a liquid-phase solvent composition and a steam contact step in which after the solvent contact step, the article to be cleaned is exposed to steam generated by evaporating the solvent composition.

From the above-described reason, a proportion of a content of HCFO-1233yd(Z) to a total amount of HCFO-1233yd is preferably 80 to 100 mass %, and more preferably 90 to 100 mass %. As long as the proportion is in the above range, the composition change of the solvent composition is hardly caused, which allows stable use thereof. However, an upper limit value of the proportion of the content of HCFO-1233yd(Z) is more preferably about 99.9 mass % to the total amount of HCFO-1233yd from the viewpoint of suppressing an increase in a manufacturing cost due to a distillation separation of the Z-isomer and the E-isomer of HCFO-1233yd, or the like.

HCFO-1233yd can be manufactured by subjecting, for example, industrially stably obtainable HCFC-244ca to a dehydrofluorination reaction. According to this method, HCFO-1233yd is produced by the dehydrofluorination reaction at temperatures of 50 to 80° C., using HCFC-244ca as a raw material and using potassium hydroxide or sodium hydroxide as a reactant.

In the produced HCFO-1233yd, HCFO-1233yd(Z) and HCFO-1233yd(E) which are a structural isomer exist, and in this manufacturing method, HCFO-1233yd(Z) is produced more than HCFO-1233yd(E). These isomers can be separated into HCFO-1233yd(Z) and HCFO-1233yd(E) in a purification process thereafter.

Note that in the solvent composition of the present invention, a roughly purified product of HCFO-1233yd which is obtained by appropriately purifying the reaction solution including HCFO-1233yd produced in the above and includes the component difficult to separate from HCFO-1233yd other than HCFO-1233yd in the range in which the effect of the present invention is not impaired, for example, by an amount which is 10 mass % or less and preferably 5 mass % or less with respect to the total amount of the solvent composition may be used. If the roughly purified product of HCFO-1233yd is used, a cost of the distillation separation or the like is reduced, which is preferable.

Thus, as the component which is incorporated into the solvent composition in a manner in which it is included in the roughly purified product of HCFO-1233yd, and is difficult to separate from HCFO-1233yd, for example, there can be cited 1-chloro-3,3-difluoro-1-propyne as a by-product to be obtained by further subjecting HCFO-1233yd to the dehydrofluorination reaction. If 1-chloro-3,3-difluoro-1-propyne is included in the solvent composition, the proportion of a content of 1-chloro-3,3-difluoro-1-propyne in the solvent composition is preferably 0.0001 to 0.1 mass %, and more preferably 0.0001 to 0.001 mass % to the total amount of HCFO-1233yd from the viewpoint of stability and a separation cost.

(HCFC-244ca)

HCFC-244ca is a compound which is used as a raw material when HCFO-1233yd is manufactured as described above, for example, can be industrially stably obtained by the later-described method and is soluble in HCFO-1233yd. HCFC-244ca is considered to have a property as HCFC and at the same time, have a function as a stabilizer suppressing decomposition of HCFO-1233yd(Z) and HCFO-1233yd(E) and stabilizing them by an effect which is not necessarily clear but is presumed to be capture of radicals.

Note that in this description, solubility of a certain substance in HCFO-1233yd means a property capable of dissolving the substance uniformly without causing a two-layer separation and turbidity by mixing it with HCFO-1233yd and stirring it at the normal temperature (25° C.) so as to become a desired concentration.

Further, the stability in the solvent composition of the present invention can be evaluated by, for example, providing a difference between an initial pH of the solvent composition and a pH after retaining the solvent composition for a certain period as an index. Note that the pH of the solvent composition in the present invention means a pH of a water layer being an upper layer when the solvent composition and pure water having a pH of 7 are mixed and shaken for a predetermined time, and thereafter left still to separate into two layers. A specific measurement condition of the pH can employ a condition mentioned in a section on a pH measurement mentioned in the later-described "EXAMPLES".

In the solvent composition of the present invention containing HCFC-244ca with HCFO-1233yd, for example, it is possible to suppress a difference in pH measured before and after retaining the solvent composition at the boiling point (about 54° C.) of HCFO-1233yd(Z) for seven days to 1.5 or less. Note that regulating an amount of HCFC-244ca with respect to HCFO-1233yd in the solvent composition also makes it possible to set the difference in pH in a case of evaluation similar to that in the above to 1.0 or less or "0" (zero).

The content of HCFC-244ca in the solvent composition of the present invention is an amount in which HCFO-1233yd is capable of exhibiting the above-described ability as a solvent and the stabilization of HCFO-1233yd is kept, namely, an amount which is 0.0001 to 1 mass % with respect to the total of the content of HCFO-1233yd and the content of HCFC-244ca. The proportion of the content of HCFC-244ca is preferably 0.0005 to 0.1 mass %, and more preferably 0.01 to 0.05 mass % to the total of the content of HCFO-1233yd and the content of HCFC-244ca.

Since HCFC-244ca and HCFO-1233yd, particularly, HCFO-1233yd(Z) are close to each other in the boiling points as described above, in the solvent composition of the present invention including these, even in uses for which it is repeatedly used while being accompanied by the phase change, the decomposition of HCFO-1233yd is suppressed and the composition change is hardly caused, which allows the stable use.

HCFC-244ca is a compound which is known as a production raw material or an intermediate of a fluorine-containing compound, and can be easily obtained. An obtaining method of HCFC-244ca is not particularly limited, for example, HCFC-244ca can be manufactured by a method in which 2,2,3,3-tetrafluoropropanol (TFPO) is chlorinated by thionyl chloride ($SOCl_2$) under the presence of N,N-dimethylformamide (DMF). This method can be performed in a liquid phase or in a gas phase.

As HCFC-244ca, HCFC-244ca isolated from a reaction solution to be obtained by the above-described method may be used, or a roughly purified product of HCFC-244ca including a component difficult to separate from HCFC-244ca other than HCFC-244ca in the range in which the effect of the present invention is not impaired, for example, by an amount which is 10 mass % or less and preferably 5 mass % or less with respect to the total amount of the solvent composition may be used.

Further, when HCFO-1233yd is manufactured using HCFC-244ca as the raw material in the above, the reaction solution including the obtained HCFO-1233yd normally includes HCFC-244ca which is an unreacted raw material as the component difficult to separate from HCFO-1233yd. As described above, the boiling point of HCFC-244ca is about 53° C. and close to the boiling point of HCFO-1233yd(Z), and therefore when HCFO-1233yd is used as HCFO-1233yd (Z) or as an isomer mixture of HCFO-1233yd, in particular, HCFC-244ca can be included in the roughly purified product.

Accordingly, it is also possible to separate a mixture which includes HCFO-1233yd and HCFC-244ca together and in which a content of a component other than these is reduced to an amount in which the effect of the present invention is not impaired from the reaction solution to be obtained by the above-described method, and it is also possible to use the mixture as it is as the solvent composition of the present invention.

(Optional Component)

The solvent composition of the present invention may contain components (hereinafter, simply referred to as "other component") other than HCFO-1233yd, HCFC-244ca, and the above-described component which is produced in the manufacturing process of HCFO-1233yd or HCFC-244ca and is difficult to separate from HCFO-1233yd or HCFC-244ca in the range in which the effect of the present invention is not impaired with HCFO-1233yd and HCFC-244ca. The other components may be components (however, HCFC-244ca is excluded, and hereinafter, referred to as "other solvent") which are used depending on various purposes such as enhancing of the solubility and regulating of an evaporation rate, are soluble in HCFO-1233yd, and function as a solvent other than HCFO-1233yd, for example.

Further, the other components may be stabilizers (hereinafter, referred to as "other stabilizer") other than HCFC-244ca stabilizing HCFO-1233yd, for example.

As the other stabilizers, there can be cited at least one selected from a group consisting of phenols, ethers, epoxides, amines, alcohols, and hydrocarbons. The stabilizer may be one or a combination of two or more.

As the phenols, phenol, 1,2-benzendiol, 2,6-di-tert-butyl-4-methylphenol, m-cresol, 2-isopropyl-5-methylphenol, α-tocopherol, and 2-methoxyphenol are preferable.

As the ethers, cyclic ethers having 4 to 6 members are preferable, and among them, 1,4-dioxane, 1,3-dioxane, 1,3,5-trioxane, 2-methylfuran, and tetrahydrofuran are preferable.

As the epoxides, 1,2-propylene oxide, 1,2-butylene oxide, and butyl glycidyl ether are preferable.

As the amines, alkylamine and cyclic amines are preferable, and among them, pyrrole, N-methylpyrrole, 2-methylpyridine, n-propylamine, diisopropylamine, N-methylmorpholine, and N-ethylmorpholine are preferable.

As the alcohols, methanol, ethanol, isopropyl alcohol, and 2-propyne-1-ol which are linear or branched-chained alcohols having 1 to 3 carbon atoms are preferable.

As the hydrocarbons, regarding saturated hydrocarbons, n-pentane, cyclopentane, n-hexane, cyclohexane, and n-heptane are preferable. Regarding unsaturated hydrocarbon, 2-methyl-2-butene, 2-methyl-1-pentene, 2-methyl-2-pentene, 3-ethyl-2-butene, 2,3-dimethyl-2-butene, 2,4,4-trimethyl-1-pentene, and 2,4,4-trimethyl-2-pentene are preferable.

As the other stabilizers, among these in terms of stability, 2-methyl-1-pentene, 2-methyl-2-pentene, 3-ethyl-2-butene, 2,3-dimethyl-2-butene, 2,4,4-trimethyl-1-pentene, 2,4,4-trimethyl-2-pentene, N-methylpyrrole, and 2-propyne-1-ol are further preferable.

When the solvent composition of the present invention is in contact with copper or a copper alloy, it may contain nitro compounds and triazoles in order to avoid corrosion of the above metals.

A content of the other components in the solvent composition of the present invention is appropriately regulated depending on types of the other components in the range in which the effect of the present invention is not impaired. A proportion of the content of the other components is preferably about 1 mass % or less and more preferably 0.1 mass % or less for each of the components to the total amount of the solvent composition. Further, a total of the content of the other components is preferably 10 mass % or less, and more preferably 1 mass % or less.

The solvent composition of the present invention is a stable solvent composition which is excellent in solubility of various organic substances and excellent in detergency, and has no adverse effect on a global environment and is stabilized to suppress decomposition, and the solvent composition is preferably used for cleaning uses such as degreasing cleaning, flux cleaning, precision cleaning, and dry cleaning. In addition, the solvent composition of the present invention can be used in uses for which a coating film-forming composition is produced by dissolving a lubricant such as a silicone-based lubricant or a fluorine-based lubricant, an antirust made from a mineral oil or a synthetic oil, a moisture-proof coating agent for conducting water repellent treatment, or an antifouling coating agent such as a fingerprint removing/preventing agent for conducting antifouling treatment and a coating film is formed by applying the coating film-forming composition on an article surface. Moreover, the solvent composition of the present invention is suitable also as a heat transfer fluid for heating or cooling an article.

The articles to which the solvent composition of the present invention is applicable can be widely used for electronic components such as a capacitor, a diode, and a substrate on which these have been mounted, optical components such as a lens and a polarizing plate, automotive parts such as a fuel injection needle to be used for an engine unit and a gear of a drive unit in an automobile, parts of a drive unit to be used for an industrial robot, machine parts such as exterior parts, a carbide tool to be used for a machine tool such as a cutting tool, and the like. Moreover, as materials to which the solvent composition of the present invention is applicable, a wide range of materials such as metal, plastic, elastomer, glass, ceramics, and fabric can be cited, and among them, the solvent composition is suitable for metals such as iron, copper, nickel, gold, silver, and platinum, a sintered metal, glass, a fluorocarbon resin, and engineering plastic such as PEEK.

<Cleaning Method>

A cleaning method of the present invention is a method of cleaning extraneous matter adhering to an article to be cleaned by using the above-described solvent composition of the present invention, and is characterized by bringing the solvent composition of the present invention and the article to be cleaned into contact with each other.

In the cleaning method of the present invention, as the extraneous matter to be removed by cleaning, there can be cited flux; processing oils such as a cutting oil, a quenching oil, a rolling oil, a lubricating oil, a machine oil, a presswork oil, a stamping oil, a drawing oil, an assembly oil, and a wire drawing oil; a release agent; dust, and the like adhering to various articles to be cleaned. Because the present solvent composition is more excellent in solubility of the processing oil compared with HFC and HFE which are conventional solvent compositions, and the like, it is preferably used for cleaning of the processing oil.

Further, the solvent composition of the present invention is applicable to cleaning of the articles to be cleaned made of various materials such as metal, plastic, elastomer, glass, ceramics, and composite materials of these, and a fabric made of natural fiber or synthetic fiber. Here, as a more specific example of the articles to be cleaned, there can be cited fiber products, medical appliances, electric equipment, precision instruments, optical articles, their parts, and the like. As a specific example of the electric equipment, the precision instruments, the optical articles, and their parts, there can be cited an IC, a capacitor, a printed-circuit board, a micromotor, a relay, a bearing, an optical lens, a glass substrate, and the like.

The cleaning method of the article to be cleaned using the solvent composition of the present invention is not particularly limited except to bring the solvent composition of the present invention and the article to be cleaned into contact with each other. The contact makes it possible to remove dirt adhering to a surface of the article to be cleaned. As a specific cleaning method, for example, it is sufficient to employ manual cleaning, immersion cleaning, spray cleaning, immersion-oscillation cleaning, immersion ultrasonic cleaning, steam cleaning, methods by combining these, and the like. Cleaning conditions such as contact time, the number of times, and a temperature of the solvent composition of the present invention at a time of cleaning in these cleaning methods may be appropriately selected depending on the cleaning methods. Further, also regarding a cleaning apparatus, the publicly known one can be appropriately selected depending on each of the cleaning methods. As long as the solvent composition of the present invention is used for these cleaning methods, it is possible to repeatedly use it for a long period while maintaining detergency with almost no decomposition of the components.

The cleaning method of the present invention is applicable to, for example, a cleaning method having a solvent contact step in which the article to be cleaned is brought into contact with a liquid-phase solvent composition and a steam contact step in which after the solvent contact step, the article to be cleaned is exposed to steam generated by evaporating the solvent composition. As the cleaning apparatus applicable to such a cleaning method and the cleaning methods, for example, a cleaning method and a cleaning apparatus indicated in International Publication WO 2008/149907 can be cited.

FIG. 1 is a view schematically illustrating one example of a cleaning apparatus similar to the cleaning apparatus which carries out the cleaning method having the above-described solvent contact step and steam contact step and is indicated in International Publication WO 2008/149907. A cleaning apparatus 10 includes a cleaning tank 1, a rinse tank 2, and a steam generation tank 3 in each of which a solvent composition L is housed. Moreover, the cleaning apparatus 10 includes, above these tanks, a steam zone 4 which is filled with steam generated from the solvent composition L, cooling tubes 9 which cool the steam, and a water separation tank 5 for subjecting the solvent composition L obtained by being condensed by the cooling tubes 9 and water adhering to the cooling tubes to a stationary separation. In actual cleaning, an article to be cleaned D is put in a dedicated jig or basket, or the like, and the cleaning is completed while moving the article to be cleaned D in order of the cleaning tank 1, the rinse tank 2, and a steam zone 43 immediately above the steam generation tank 3 in the cleaning apparatus 10.

A heater 7 and an ultrasonic vibrator 8 are included in a lower portion of the cleaning tank 1. In the cleaning tank 1, a temperature of the solvent composition L is raised by heating with the heater 7, physical force is imparted to the article to be cleaned D by cavitation generated by the ultrasonic vibrator 8 while controlling a constant temperature, and dirt adhering to the article to be cleaned D is removed by cleaning. At this time, as the physical force, other than an ultrasonic wave, any method which has been employed for previous cleaning machines, such as oscillation or a submerged jet of the solvent composition L, may be used. Note that in the cleaning of the article to be cleaned D in the cleaning tank 1, the ultrasonic vibration is not essential, and the cleaning may be performed without the ultrasonic vibration as necessary.

In the rinse tank 2, by immersing the article to be cleaned D in the solvent composition L, dirt components adhering to the article to be cleaned D in a state of dissolving in the solvent composition L are removed. The cleaning apparatus 10 has a design in which an overflow of the solvent composition L housed in the rinse tank 2 flows into the cleaning tank 1. Further, the cleaning tank 1 includes a pipe 11 which feeds the solvent composition L to the steam generation tank 3 in order to prevent a solution level from becoming equal to or more than a predetermined height.

In a lower portion of the steam generation tank 3, a heater 6 which heats the solvent composition L in the steam generation tank 3 is included. The solvent composition L housed in the steam generation tank 3 is boiled by heating with the heater 6, part or the whole of its composition becomes steam to rise upward as illustrated by arrows 13, and the steam zone 43 filled with the steam is formed immediately above the steam generation tank 3. The article to be cleaned D for which the cleaning in the rinse tank 2 has been completed is transported to the steam zone 43 and cleaned by the steam through an exposure to the steam (steam contact step).

Further, in the cleaning apparatus 10, an upper space of the tanks is used in common as the steam zone 4. The steam generated from the cleaning tank 1, the rinse tank 2, and the steam generation tank 3 is collected from the steam zone 4 as the solvent composition L by being cooled and condensed by the cooling tubes 9 provided in an upper portion of a wall surface of the cleaning apparatus 10. Thereafter, the aggregated solvent composition L is housed in the water separation tank 5 via a pipe 14 connecting the cooling tubes 9 and the water separation tank 5. In the water separation tank 5, water mixing in the solvent composition L is separated. The solvent composition L from which the water has been separated is returned to the rinse tank 2 through a pipe 12 connecting the water separation tank 5 and the rinse tank 2. In the cleaning apparatus 10, such a mechanism allows a reduction in an evaporation loss of the solvent composition.

When cleaning is performed in the cleaning apparatus 10 by using the solvent composition of the present invention, a temperature of the solvent composition of the present invention in the cleaning tank 1 is preferably set to 25° C. or more and less than the boiling point of the solvent composition. As long as the temperature is in the above-described range, it is possible to easily perform the degreasing cleaning of a processing oil or the like, and a cleaning effect by the ultrasonic wave is high. Further, a temperature of the solvent composition of the present invention in the rinse tank 2 is preferably 10 to 45° C. As long as the temperature is in the above-described range, a difference between a temperature of the article and a temperature of the steam of the solvent composition can be obtained sufficiently in a steam cleaning step, and therefore a sufficient amount of the solvent composition can be condensed on an article surface for steam cleaning, thereby resulting in a high rinsing effect. In addition, the temperature of the solvent composition of the present invention in the cleaning tank 1 is preferably higher than the temperature of the solvent composition in the rinse tank 2 in terms of detergency.

<Dry Cleaning Method>

Next, a case of using the solvent composition of the present invention for removal cleaning of dirt of various clothing will be described. The solvent composition of the present invention is suitable as a cleaning solvent for the clothing, namely, a dry cleaning solvent.

There can be cited cleaning and removing of dirt adhering to clothing such as a shirt, a sweater, a jacket, a skirt, trousers, a windbreaker, gloves, a muffler, and a stole, as a dry cleaning application using the solvent composition of the present invention.

Moreover, the solvent composition of the present invention is applicable to dry cleaning of the clothing made of fibers such as cotton, hemp, wool, rayon, polyester, acryl, and nylon.

Further, it is found that since HCFO-1233yd included in the solvent composition of the present invention includes a chlorine atom in its molecule, it has high solubility of the dirt and has cleaning power nearly equal to that of HCFCs such as HCFC-225 (dichloropentafluoropropane) having a wide range of solvency, with respect to oil and fat dirt.

Moreover, when the solvent composition of the present invention is used as the dry cleaning solvent, it is possible to compound soap in order to enhance the ability to remove water-soluble dirt such as sweat or mud, and to use the resultant product as a dry cleaning solvent composition. The soap indicates a surfactant to be used for the dry cleaning, and a cationic, nonionic, anionic, or ampholytic surfactant or the like is preferably used. It is found that since HCFO-1233yd has a chlorine atom in its molecule, it has a wide range of solubility to various organic compounds, and it is not required to optimize the soap depending on the solvent as HFEs and HFCs are required, which allows use of various soaps. Hence, the dry cleaning solvent composition using the solvent composition of the present invention can include at least one type of the surfactant selected from a group consisting of the cationic surfactant, the nonionic surfactant, the anionic surfactant, and the ampholytic surfactant.

As a specific example of the soaps, there can be cited a quaternary ammonium salt such as dodecyldimethylammonium chloride or trimethylammonium chloride as the cationic surfactant. There can be cited a surfactant such as polyoxyalkylene nonylphenyl ether, polyoxyalkylene alkyl ether, fatty acid alkanolamide, glycerin fatty acid ester, sorbitan fatty acid ester, sucrose fatty acid ester, propylene glycol fatty acid ester, or ester of phosphoric acid and fatty acid as the nonionic surfactant. There can be cited an alkyl sulfate such as a polyoxyethylene alkyl sulfate, a carboxylate such as a fatty acid salt (so-called soap), or a sulfonate such as an α-olefin sulfonate or a lauryl sulfate as the anionic surfactant. There can be cited a betaine compound such as alkylbetaine as the ampholytic surfactant.

A proportion of the content of the soap in the dry cleaning solvent composition is 0.01 to 10 mass %, preferably 0.1 to 5 mass %, and further preferably 0.2 to 2 mass % to a total amount of the solvent composition included in the dry cleaning solvent composition.

According to the above-explained cleaning method of the present invention, using the above-described solvent composition of the present invention suppresses decomposition of the solvent composition and allows repeated cleaning for a long period. In addition, as long as the solvent composition of the present invention is used, it is also possible to appropriately combine regeneration operations such as distillation regeneration and filtration regeneration, gas recovery in which scattered steam of the solvent composition is recovered, and the like without problems.

<Forming Method of Coating Film>

The solvent composition of the present invention can be used for a solvent (dilution coating solvent) for dilution coating of a nonvolatile organic compound. That is, a method of forming a coating film of the present invention is characterized by dissolving a nonvolatile organic compound in the above-described solvent composition of the present invention to prepare a coating film-forming composition and evaporating the solvent composition after applying the coating film-forming composition on an article to be coated, to form a coating film consisting of the nonvolatile organic compound.

Here, the nonvolatile organic compound in the present invention means the one which has a boiling point higher than that of the solvent composition of the present invention and in which the organic compound still remains on a surface even after evaporation of the solvent composition. As the nonvolatile organic compounds, specifically, there can be cited a lubricant for imparting lubricity to an article, an antirust for imparting an anti-rust effect to metal parts, a moisture-proof coating agent for imparting water repellency to an article, an antifouling coating agent such as a fingerprint removing/preventing agent for imparting antifouling ability to an article, and the like. In the method of forming the coating film of the present invention, it is preferable to use the lubricant as the nonvolatile organic compound from the viewpoint of solubility.

The lubricant means the one which is used for reducing friction on a contact surface and preventing generation of heat and abrasion damage when two members move in a state in which their surfaces are brought into contact with each other. The lubricant may be any form of liquid (oil), semisolid (grease), and solid.

As the lubricant, in terms of excellent solubility to HCFO-1233yd, a fluorine-based lubricant or a silicone-based lubricant is preferable. Note that the fluorine-based lubricant means a lubricant having a fluorine atom in a molecule. Further, the silicone-based lubricant means a lubricant including silicone.

The lubricant included in the coating film-forming composition may be one or a combination of two or more. Each of the fluorine-based lubricant and the silicone-based lubricant may be used alone, or they may be used in combination.

As the fluorine-based lubricant, there can be cited a fluorine-based oil, fluorine-based grease, or a fluorine-based solid lubricant such as resin powder of polytetrafluoroethylene. As the fluorine-based oil, a low polymer of perfluoropolyether or chlorotrifluoroethylene is preferable. As commercial products of the fluorine-based oil, for example, there can be cited product names "Krytox (registered trademark)

GPL102" (manufactured by Du Pont Co., Ltd.), "DAIFLOIL #1", "DAIFLOIL #3", "DAIFLOIL #10", "DAIFLOIL #20" "DAIFLOIL #50", "DAIFLOIL #100", "DEMNUM S-65" (these are manufactured by Daikin Industries, Ltd.), and the like.

As the fluorine-based grease, the one in which the fluorine-based oil such as the low polymer of perfluoropolyether or chlorotrifluoroethylene is used as a base oil and powder of polytetrafluoroethylene or other thickeners are compounded is preferable. As commercial products of the fluorine-based grease, for example, there can be cited product names "Krytox (registered trademark) grease 240AC" (manufactured by Du Pont Co., Ltd.), "DAIFLOIL grease DG-203", "DEMNUM L65", "DEMNUM L100", "DEMNUM L200", (these are manufactured by Daikin Industries, Ltd.), "Sumitec F936" (manufactured by SUMICO LUBRICANT CO., LTD.), "Molykote (registered trademark) HP-300", "Molykote (registered trademark) HP-500", "Molykote (registered trademark) HP-870", "Molykote (registered trademark) 6169" (these are manufactured by Dow Corning Toray Co., Ltd.), and the like.

As the silicone-based lubricant, a silicone oil or silicone grease can be cited. As the silicone oils, a dimethyl silicone, a methyl hydrogen silicone, a methyl phenyl silicone, a cyclic dimethyl silicone, an amine group-modified silicone, a diamine group-modified silicone, and a modified silicone oil in which an organic group has been introduced into a side chain or a terminal are preferable. As commercial products of the silicone oil, for example, there can be cited product names "Shin-Etsu Silicone KF-96", "Shin-Etsu Silicone KF-965", "Shin-Etsu Silicone KF-968", "Shin-Etsu Silicone KF-99", "Shin-Etsu Silicone KF-50", "Shin-Etsu Silicone KF-54", "Shin-Etsu Silicone HIVAC F-4", "Shin-Etsu Silicone HIVAC F-5", "Shin-Etsu Silicone KF-56A", "Shin-Etsu Silicone KF-995", "Shin-Etsu Silicone KF-868", "Shin-Etsu Silicone KF-859" (these are manufactured by Shin-Etsu Chemical Co., Ltd.), "SH200" (manufactured by Dow Corning Toray Co., Ltd.), and the like.

As the silicone grease, products in which the various silicone oils cited above are used as a base oil and a thickener such as a metal soap or various additives are compounded are preferable. As commercial products of the silicone grease, for example, there can be cited product names "Shin-Etsu Silicone G-30 Series", "Shin-Etsu Silicone G-40 Series", "Shin-Etsu Silicone FG-720 Series", "Shin-Etsu Silicone G-411", "Shin-Etsu Silicone G-501", "Shin-Etsu Silicone G-6500", "Shin-Etsu Silicone G-330", "Shin-Etsu Silicone G-340", "Shin-Etsu Silicone G-350", "Shin-Etsu Silicone G-630" (these are manufactured by Shin-Etsu Chemical Co., Ltd.), "Molykote (registered trademark) SH33L", "Molykote (registered trademark) 41", "Molykote (registered trademark) 44", "Molykote (registered trademark) 822M", "Molykote (registered trademark) 111", "Molykote (registered trademark) grease for high vacuum", "Molykote (registered trademark) heat diffusion compound" (these are manufactured by Dow Corning Toray Co., Ltd.), and the like.

Further, as the one which can be exemplified as the fluorine-based lubricant and as the silicone-based lubricant, there can be cited a fluorosilicone oil which is a modified silicone oil in which a fluoroalkyl group has been substituted for a terminal or a side chain. As commercial products of the fluorosilicone oil, for example, there can be cited product names "Unidyne (registered name) TG-5601" (manufactured by Daikin Industries, Ltd.), "Molykote (registered trademark) 3451", "Molykote (registered trademark) 3452", (these are manufactured by Dow Corning Toray Co., Ltd.), "Shin-Etsu Silicone FL-5", "Shin-Etsu Silicone X-22-821", "Shin-Etsu Silicone X-22-822", "Shin-Etsu Silicone FL-100" (these are manufactured by Shin-Etsu Chemical Co., Ltd.), and the like.

These lubricants can be used as a coating film for, for example, industrial equipment, tray parts for a CD and a DVD in a personal computer and an audiovisual apparatus, household appliances and office equipment such as a printer, a copier, and a flux device, and the like for which the fluorine-based lubricant is used normally as the coating film. Further, for example, they can be used for a needle and a cylinder of a syringe, medical tube parts, a metal blade, a catheter, and the like for which the silicone-based lubricant is used normally as the coating film.

The antirust means the one which is used for preventing rust of metal materials by covering a surface of metals and blocking oxygen from the metal surface which are easily oxidized by oxygen in the air to generate rust. As the antirusts, there can be cited a mineral oil, and synthetic oils such as polyol esters, polyalkylene glycols, and polyvinyl ethers.

The moisture-proof coating agent and the antifouling coating agent are the ones which are used for imparting a moisture-proof property and an antifouling property to plastic, rubber, metal, glass, a mounted circuit board, and the like. As product examples of the moisture-proof coating agent, there can be cited TOPAS 5013, TOPAS 6013, TOPAS 8007 (manufactured by Polyplastics Co., Ltd.), ZEONOR 1020R, ZEONOR 1060R (manufactured by Zeon Corporation), Apel 6011T, Apel 8008T, (manufactured by Mitsui Chemicals, Inc.), SFE-DP02H, SNF-DP20H (manufactured by AGC SEIMI CHEMICAL CO., LTD.). As product examples of the antifouling coating agent such as a fingerprint preventing agent, there can be cited OPTOOL DSX, OPTOOL DAC (manufactured by Daikin Industries, Ltd.), Fluoro Surf FG-500 (manufactured by Fluoro Technology Co., Ltd.), SR-4000A (manufactured by AGC SEIMI CHEMICAL CO., LTD.), and the like.

The coating film-forming composition is produced normally as a composition in solution form in which the nonvolatile organic compound has been dissolved in the solvent composition of the present invention. A production method of the coating film-forming composition is not particularly limited as long as it is a method of allowing the nonvolatile organic compound to be uniformly dissolved in the solvent composition of the present invention in a predetermined proportion. The coating film-forming composition basically consists of only the nonvolatile organic compound and the solvent composition of the present invention. In the following explanation, the coating film-forming composition using the lubricant as the nonvolatile organic compound is referred to as "lubricant solution". The coating film-forming compositions using other nonvolatile organic compounds are also similar.

A proportion of a content of the lubricant with respect to a total amount of the lubricant solution is preferably 0.01 to 50 mass %, more preferably 0.05 to 30 mass %, and further preferably 0.1 to 20 mass %. The remainder except the lubricant of the lubricant solution is the solvent composition. As long as the content of the lubricant is in the above-described range, a film thickness of a coating film when the lubricant solution is applied and a thickness of a lubricant coating film after drying are easily regulated in a proper range.

A content of each of the nonvolatile organic compounds such as the antirust, the moisture-proof coating agent, and the antifouling coating agent with respect to a total amount of each of solutions (coating film-forming compositions) in the coating film-forming compositions such as an antirust solution, a moisture-proof coating agent solution, and an antifouling coating agent solution is also preferably in the same range as the above-described content of the lubricant in the lubricant solution.

A coating film consisting of the nonvolatile organic compound can be formed on an article to be coated by applying the coating film-forming composition containing the above-described solvent composition and nonvolatile organic compound on the article to be coated and evaporating the solvent composition from the coating film-forming composition applied on the article to be coated.

As the articles to be coated on which the coating film of the lubricant, the antirust, the moisture-proof coating agent, the antifouling coating agent, or the like is formed, namely, the coating film-forming composition each including these is applied, the articles to be coated made of various materials such as metal, plastic, elastomer, glass, and ceramics can be employed. As specific articles, the articles explained above for each of the nonvolatile organic compounds can be cited.

As an applying method of the coating film-forming composition, for example, there can be cited applying by using a brush, applying by spraying, applying by immersing the articles in the coating film-forming composition, an applying method of bringing the coating film-forming composition into contact with an inner wall of a tube or a needle by pumping up the coating film-forming composition, or the like.

As a method of evaporating the solvent composition from the coating film-forming composition, a publicly known drying method can be cited. As the drying method, for example, air drying, drying by heating, or the like can be cited. A drying temperature is preferably 20 to 100° C.

In the method of forming the coating film of the present invention explained above, either in a state of the solvent composition of the present invention before dissolving these lubricant, antirust, moisture-proof coating agent, and antifouling coating agent, and the like, or in a state of the above-described coating film-forming composition, the use is possible with almost no decomposition in storage or in use.

<Heat Transfer Fluid and Heat Cycle System>

The solvent composition of the present invention can be used as a working fluid (heat transfer fluid) for a heat cycle system. That is, the present invention provides the heat transfer fluid including the solvent composition of the present invention. The heat transfer fluid of the present invention is applicable to the heat cycle system by which materials are heated or cooled.

As the heat cycle systems, there can be cited a Rankine cycle system, a heat pump cycle system, a refrigeration cycle system, a heat transport system, a secondary refrigerant cooling system, and the like. Hereinafter, as one example of the heat cycle system, the refrigeration cycle system will be explained.

The refrigeration cycle system is a system in which the working fluid removes heat energy from a load fluid in an evaporator, thereby cooling the load fluid and cooling it to lower temperature. The refrigeration cycle system is a system constituted of a compressor which compresses a working fluid vapor A to make it into a working fluid vapor B at high temperature and high pressure, a condenser which cools and liquefies the compressed working fluid vapor B to make it into a working fluid C at low temperature and high pressure, an expansion valve which expands the working fluid C emitted from the condenser to make it into a working fluid D at low temperature and low pressure, an evaporator which heats the working fluid D emitted from the expansion valve to make it into the working fluid vapor A at high temperature and low pressure, a pump which supplies a load fluid E to the evaporator, and a pump which supplies a fluid F to the condenser.

The heat transfer fluid of the present invention may include a component other than the solvent composition of the present invention in a range in which the effect of the present invention is not impaired, and preferably consists of only the solvent composition of the present invention. To the heat transfer fluid of the present invention, a lubricating oil can be added. For the lubricating oil, a publicly known lubricating oil to be used for the heat cycle system is used. As the lubricating oils, there can be cited an oxygenated synthetic oil (ester-based lubricating oil, ether-based lubricating oil, and the like), a fluorine-based lubricating oil, a mineral oil, a hydrocarbon-based synthetic oil, and the like.

Moreover, the heat transfer fluid of the present invention is also applicable to a secondary circulation cooling system. The secondary circulation cooling system is a system having a primary cooling device which cools a primary refrigerant consisting of ammonia or a hydrocarbon refrigerant, a secondary circulation cooling device which cools an article to be cooled by circulating a secondary refrigerant for secondary circulation cooling system (hereinafter, referred to as "secondary refrigerant"), and a heat exchanger which exchanges heat between the primary refrigerant and the secondary refrigerant and cools the secondary refrigerant. This secondary circulation cooling system allows cooling of the article to be cooled. The heat transfer fluid of the present invention is suitable for use as the secondary refrigerant.

EXAMPLES

Hereinafter, the present invention will be explained in detail by examples. The present invention is not limited to these examples. Examples 1 to 5, 8 to 12, and 15 to 19 are the examples of the solvent composition of the present invention, and Examples 6 to 7, 13 to 14, and 20 to 21 are comparative examples.

Production Example: Production of HCFC-244ca

In a two-liter four-necked flask in which a glass distillation column (a measured value of five stages in the number of stages) packed with an agitator, a Dimroth, a cooler, and a Rasching ring was placed, 1204 g (9.12 mol) of 2,2,3,3-tetrafluoropropanol (TFPO) and 12 g (0.17 mol) of N,N-dimethylformamide (DMF) were added. 1078 g (9.12 mol) of thionyl chloride was dropped and agitated at a normal temperature for 12 hours. A reactor was heated to 100° C., and reactive distillation was performed at a ratio of 5/1 of reflux time/distillation time by using a reflux timer. Distilled HCFC-244ca was neutralized by a 20 mass % aqueous potassium hydroxide solution. Recovered HCFC-244ca (purity 100%) was 979 g (6.50 mol).

Production Example: Production of 1233yd(Z) and 1233yd(E)

2000 g of HCFC-244ca was used as a raw material, 19.9 g of tetra-n-butyl ammonium chloride was put in, a reaction temperature was kept at 50° C., and 2792 g of a 40 mass % aqueous potassium hydroxide solution was dropped over 30 minutes. Thereafter, a reaction was continued for 52 hours, and an organic layer was recovered. The recovered organic layer was refined, resulting in obtaining 1520 g of purity 100 mass % HCFO-1233yd(Z) (hereinafter, simply referred to as "HCFO-1233yd(Z)") and 140 g of purity 100 mass % HCFO-1233yd(E) (hereinafter, simply referred to as "HCFO-1233yd(E)"). This preparation was repeatedly performed to produce a required amount of each of 1233yd(Z) and 1233yd(E).

Examples 1 to 5, 8 to 12, 15 to 19: Production of Solvent Composition (Example))

51 kg each of solvent compositions in Examples 1 to 5, 8 to 12, and 15 to 19 containing HCFO-1233yd(Z) and/or HCFO-1233yd(E), and HCFC-244ca as a stabilizer is prepared so as to each become a proportion of a content presented in Table 1 by using HCFC-244ca, HCFO-1233yd (Z), and HCFO-1233yd(E) obtained in the above.

Numeric values of HCFO-1233yd(Z) and HCFO-1233yd (E) presented in Table 1 are each the proportion of the content of each of the components to a total of the content of HCFO-1233yd and the content of HCFC-244ca, and numeric values of HCFC-244ca are each the proportion of the content of HCFC-244ca to a total amount of the solvent composition. Further, the solvent compositions in Examples 1 to 5, 8 to 12, and 15 to 19 are each a solvent composition consisting of only HCFO-1233yd and HCFC-244ca.

Examples 6 to 7, 13 to 14, 20 to 21: Production of Solvent Composition (Comparative Example))

51 kg each of solvent compositions in Examples 6 to 7, 13 to 14, and 20 to 21 each including HCFO-1233yd(Z), HCFO-1233yd(E), and optionally HCFC-244ca in the proportion presented in Table 1 and each consisting of only HCFO-1233yd or HCFO-1233yd and HCFC-244ca more than the upper limits is produced by using HCFO-1233yd (Z), HCFO-1233yd(E) and HCFC-244ca obtained in the above.

[Evaluation]

1. Stability Test and Metal Corrosion Resistance Test 100 g of each of the solvent compositions in Examples 1 to 21 is put in a heat-resistant glass bottle in which a test piece of a general-purpose cold-rolled steel sheet (SPCC) has been put, and retained at a boiling point (about 54° C.) of HCFO-1233yd(Z) for seven days. Table 1 presents measured results of a pH immediately after the preparation (before the test) and after the retention for seven days (after the test), and evaluation results of an appearance observation of a SPCC surface after the retention for seven days (after the test).

(pH Measurement)

40 g of the solvent compositions in each of the examples and 40 g of pure water prepared at pH 7 are put in a 200 mL-capacity separatory funnel and shaken for one minute. Thereafter, they are left still, and a water layer being an upper layer obtained by a two-layer separation is separately collected, and a pH of the water layer is measured by a pH meter (model number: HM-30R, manufactured by DDK-TOA CORPORATION).

A change in the metal surfaces before and after the test is visually evaluated by using an untested specimen of each of the metals as a comparison article. The evaluation criteria are as follows.

"S (excellent)": there is no change before and after the test.

"A (good)": a gloss has been lost after the test compared with before the test, but there is no practical problem.

"B (slightly poor)": a surface after the test slightly rusts.

"x (poor)": rust is recognized on the entire surface of the surface after the test.

TABLE 1

| Example | HCFO-1233yd(Z) HCFO-1233yd(E) HCFC-244ca Proportion (mass %) of content of each of components to total of content of HCFO-1233yd and content of HCFC-244ca | | | pH Before test | pH After test | Appearance after metal corrosion resistance test |
|---|---|---|---|---|---|---|
| 1  | 99.9999 | 0  | 0.0001 | 7.0 | 6.3 | A |
| 2  | 99.9995 | 0  | 0.0005 | 7.0 | 7.0 | S |
| 3  | 99.99   | 0  | 0.01   | 7.0 | 7.0 | S |
| 4  | 99.9    | 0  | 0.1    | 7.0 | 7.0 | S |
| 5  | 99      | 0  | 1      | 7.0 | 7.0 | S |
| 6  | 98.5    | 0  | 1.5    | 7.0 | 6.0 | B |
| 7  | 100     | 0  | —      | 7.0 | 4.6 | x |
| 8  | 94.9999 | 5  | 0.0001 | 7.0 | 6.4 | A |
| 9  | 94.9995 | 5  | 0.0005 | 7.0 | 7.0 | S |
| 10 | 94.99   | 5  | 0.01   | 7.0 | 7.0 | S |
| 11 | 94.9    | 5  | 0.1    | 7.0 | 7.0 | S |
| 12 | 94      | 5  | 1      | 7.0 | 7.0 | S |
| 13 | 93.5    | 5  | 1.5    | 7.0 | 6.0 | B |
| 14 | 95      | 5  | —      | 7.0 | 4.2 | x |
| 15 | 79.9999 | 20 | 0.0001 | 7.0 | 6.3 | A |
| 16 | 79.9995 | 20 | 0.0005 | 7.0 | 7.0 | S |
| 17 | 79.99   | 20 | 0.01   | 7.0 | 7.0 | S |
| 18 | 79.9    | 20 | 0.1    | 7.0 | 7.0 | S |
| 19 | 79      | 20 | 1      | 7.0 | 7.0 | S |
| 20 | 78.5    | 20 | 1.5    | 7.0 | 6.1 | B |
| 21 | 80      | 20 | —      | 7.0 | 3.7 | x |

From Table 1, it is found that in any of the solvent compositions in the examples of the present invention, acidification has been suppressed as compared with the comparative examples. In addition, it is found that corrosion of the metal test pieces has been suppressed in the examples rather than in the comparative examples. This makes it obvious that the solvent composition of the present invention not only achieves a stabilization effect of an excellent solvent composition but also is capable of suppressing the metal corrosion.

2. Continuous Operation Test with Cleaning Apparatus 50 kg of each of the solvent compositions in Examples 1 to 21 is put in a cleaning tank 1, a rinse tank 2, and a steam generation tank 3 of a three-tank cleaning apparatus 10 similar to that in FIG. 1, and a circulation operation is performed by each of them for 300 hours. 100 g of each of solvent compositions L in the steam generation tank 3, the cleaning tank 1, and a water separation tank 5 is collected before an operation start (initial stage) and after 10 hours, 100 hours, and 300 hours after the operation start, and chlorine ion concentrations are measured by the following method. Tables 2, 3 present the results.

(Chlorine Ion Concentration Measurement)

After putting 50 g of the collected solvent composition in a 100 mL sample bottle, 50 g of ion-exchange water is added and shaken by hand for 30 seconds, thereby extracting chlorine ions included in the solvent composition into the ion-exchange water. After standing still and separating the ion-exchange water, the chlorine ion concentration (ppm) included in the ion-exchange water is measured by an ion chromatography (ICS-1000, manufactured by Dionex Corporation).

From the obtained chlorine ion concentration measurement results, stability is evaluated by the following index. Note that any of concentrations in the index of the evaluation is a chlorine ion concentration.

"S (excellent)": less than 10 mass ppm

"A (good)": 10 mass ppm or more and less than 50 mass ppm

"B (slightly poor)": 50 mass ppm or more and less than 100 mass ppm

"x (poor)": 100 ppm or more

TABLE 2

| | | Stability evaluation setting chlorine ion concentration as index | | | |
|---|---|---|---|---|---|
| Example | Collection point | Initial stage | After 10 hours | After 100 hours | After 300 hours |
| 1 | Steam generation tank | S | S | A | A |
| | Cleaning tank | S | S | S | S |
| | Water separation tank | S | S | S | S |
| 2 | Steam generation tank | S | S | S | S |
| | Cleaning tank | S | S | S | S |
| | Water separation tank | S | S | S | S |
| 3 | Steam generation tank | S | S | S | S |
| | Cleaning tank | S | S | S | S |
| | Water separation tank | S | S | S | S |
| 4 | Steam generation tank | S | S | S | S |
| | Cleaning tank | S | S | S | S |
| | Water separation tank | S | S | S | S |
| 5 | Steam generation tank | S | S | S | S |
| | Cleaning tank | S | S | S | S |
| | Water separation tank | S | S | S | S |
| 6 | Steam generation tank | S | S | A | B |
| | Cleaning tank | S | S | A | B |
| | Water separation tank | S | S | S | A |

TABLE 2-continued

| | | Stability evaluation setting chlorine ion concentration as index | | | |
|---|---|---|---|---|---|
| Example | Collection point | Initial stage | After 10 hours | After 100 hours | After 300 hours |
| 7 | Steam generation tank | S | A | B | x |
| | Cleaning tank | S | S | A | B |
| | Water separation tank | S | S | A | B |
| 8 | Steam generation tank | S | S | A | A |
| | Cleaning tank | S | S | S | S |
| | Water separation tank | S | S | S | S |
| 9 | Steam generation tank | S | S | S | S |
| | Cleaning tank | S | S | S | S |
| | Water separation tank | S | S | S | S |
| 10 | Steam generation tank | S | S | S | S |
| | Cleaning tank | S | S | S | S |
| | Water separation tank | S | S | S | S |
| 11 | Steam generation tank | S | S | S | S |
| | Cleaning tank | S | S | S | S |
| | Water separation tank | S | S | S | S |
| 12 | Steam generation tank | S | S | S | S |
| | Cleaning tank | S | S | S | S |
| | Water separation tank | S | S | S | S |
| 13 | Steam generation tank | S | S | A | B |
| | Cleaning tank | S | S | A | A |
| | Water separation tank | S | S | S | A |
| 14 | Steam generation tank | S | A | B | x |
| | Cleaning tank | S | S | A | B |
| | Water separation tank | S | S | A | B |

TABLE 3

| | | Stability evaluation setting chlorine ion concentration as index | | | |
|---|---|---|---|---|---|
| Example | Collection point | Initial stage | After 10 hours | After 100 hours | After 300 hours |
| 15 | Steam generation tank | S | S | A | A |
| | Cleaning tank | S | S | S | S |
| | Water separation tank | S | S | S | S |
| 16 | Steam generation tank | S | S | S | S |
| | Cleaning tank | S | S | S | S |
| | Water separation tank | S | S | S | S |
| 17 | Steam generation tank | S | S | S | S |
| | Cleaning tank | S | S | S | S |
| | Water separation tank | S | S | S | S |
| 18 | Steam generation tank | S | S | S | S |
| | Cleaning tank | S | S | S | S |
| | Water separation tank | S | S | S | S |
| 19 | Steam generation tank | S | S | S | S |
| | Cleaning tank | S | S | S | S |
| | Water separation tank | S | S | S | S |
| 20 | Steam generation tank | S | S | A | B |
| | Cleaning tank | S | S | S | A |
| | Water separation tank | S | S | S | A |
| 21 | Steam generation tank | S | A | B | x |
| | Cleaning tank | S | S | A | B |
| | Water separation tank | S | S | A | B |

From Tables 2, 3, it is found that in any of the examples of the present invention, acidification is suppressed for a long stretch of time and occurrence of chloride ions due to decomposition is suppressed as compared with the solvent compositions in the comparative examples. From this, it is found that the solvent composition of the present invention is excellent in long-term stability in an actual cleaning apparatus.

3. Evaluation of Cleaning Ability

The above-described solvent compositions in Examples 1 to 5, 8 to 12, and 15 to 19 (examples) and Examples 6 to 7, 13 to 14, and 20 to 21 (comparative examples) are produced further, and each of the following cleaning tests is performed.

[Cleaning Test A]

After immersing a test piece (25 mm×30 mm×2 mm) of stainless steel SUS-304 in a product name "Daphne Magplus HT-10" (manufactured by Idemitsu Kosan Co., Ltd.) which is a cutting oil, the test piece is immersed in 50 mL of the solvent composition in each of Examples 1 to 21 for one minute and pulled up, and degrees to which the cutting oil has been removed are observed. Evaluation of detergency is performed by the following criteria.

"S (excellent)": the cutting oil is completely removed.
"A (good)": the cutting oil is almost removed.
"B (slightly poor)": the cutting oil remains in trace amounts.
"x (poor)": the cutting oil considerably remains.

[Cleaning Test B]

A test is conducted similarly to the cleaning test A except to use a product name "Daphne Magplus AM20" (manufactured by Idemitsu Kosan Co., Ltd.) as a cutting oil, and detergency is evaluated by the same criteria.

[Cleaning Test C]

A test is conducted similarly to the cleaning test A except to use a product name "Daphne Magplus HM25" (manufactured by Idemitsu Kosan Co., Ltd.) as a cutting oil, and detergency is evaluated by the same criteria.

[Cleaning Test D]

A test is conducted similarly to the cleaning test A except to use a product name "G-6318FK" (manufactured by NIHON KOHSAKUYU CO., LTD.) as a cutting oil, and detergency is evaluated by the same criteria.

In the cleaning tests A to D, any evaluation related to Examples 1 to 21 is S (excellent).

It is found from the above-described results that the solvent compositions in the examples of the present invention in Examples 1 to 5, 8 to 12, and 15 to 19 are capable of sufficiently cleaning and removing the cutting oil and have excellent detergency similarly to those in Examples 6 to 7, 13 to 14, and 20 to 21 to which a stabilizer is not added, in any cleaning test.

4. Evaluation as Dilution Coating Solvent for Lubricant (Evaluation as Dilution Coating Solvent for Fluorine-based Lubricant)

The above-described solvent compositions in Examples 1 to 5, 8 to 12, and 15 to 19 (examples) and Examples 6 to 7, 13 to 14, and 20 to 21 (comparative examples) are produced further, and each of the solvent compositions and a product name "Krytox (registered trademark) GPL102" (manufactured by Du Pont Co., Ltd., fluorine-based oil) which is a fluorine-based lubricant are mixed with each other to prepare a lubricant solution in which an amount of the fluorine-based lubricant is 0.5 mass % with respect to a total amount of the solution.

Next, on a surface of an aluminum deposited sheet in which aluminum has been deposited on a sheet made of iron, the obtained lubricant solutions are each applied in a thickness of 0.4 mm and air-dried under a condition of 19° C. to 21° C., thereby each forming a lubricant coating film on the aluminum deposited sheet surface. Evaluation as lubricant dilution coating solvents of the solvent composition of the present invention is performed as follows. As the results of the evaluation of each of the lubricant dilution coating solvents, in Examples 1 to 21, any evaluation is S (excellent).

[Evaluation Method]
[Dissolved State]

A dissolved state of the lubricant solution using the solvent composition in each of the examples is visually confirmed to be evaluated by the following criteria.

"S (excellent)": immediately uniformly dissolved to become transparent.
"A (good)": if shaken, uniformly dissolved to become transparent.
"B (slightly poor)": slightly cloudy.
"x (poor)": cloudy or phase-separated.

[Coating Film State]

A state of the lubricant coating film formed by the lubricant solution using the solvent composition in each of the examples is visually confirmed to be evaluated by the following criteria.

"S (excellent)": a uniform coating film is formed.
"A (good)": an almost uniform coating film is formed.
"B (slightly poor)": nonuniformity is partially seen on the coating film.
"x (poor)": nonuniformity is considerably seen on the coating film.

[Drying Property]

In a drying property of the lubricant solution when the lubricant coating film is formed by the lubricant solution using the solvent composition in each of the examples, the drying property is evaluated by the following criteria.

"S (excellent)": the solvent composition immediately evaporates.
"A (good)": the solvent composition evaporates within ten minutes.
"B (possible)": the solvent composition evaporates over ten minutes within one hour.
"x (poor)": the solvent composition remains even when one hour has passed.

(Evaluation as Dilution Coating Solvent for Silicone-based Lubricant)

The above-described solvent compositions in Examples 1 to 5, 8 to 12, and 15 to 19 (examples) and Examples 6 to 7, 13 to 14, and 20 to 21 (comparative examples) are produced further, and each of the solvent compositions and a product name "Shin-Etsu Silicone KF-96-50CS" (manufactured by Shin-Etsu Chemical Co., Ltd., silicone oil) which is a silicone-based lubricant are mixed with each other to prepare a lubricant solution in which an amount of the silicone-based lubricant is 3 mass % with respect to a total amount of the solution.

Thereafter, lubricant coating films are each formed on a surface of an aluminum deposited sheet in a similar manner to that of the coating of the lubricant solution of the fluorine-based lubricant. The evaluation method and the evaluation criteria are similar to the evaluation in the coating of the lubricant solution of the fluorine-based lubricant. As the results of the evaluation of each of the lubricant dilution coating solvents, in Examples 1 to 21, any evaluation is S (excellent).

It is found from the above-described results that the solvent compositions in the examples of the present invention in Examples 1 to 5, 8 to 12, and 15 to 19 are excellent in solubility of the lubricant and have a sufficient drying property, and are capable of simply forming a uniform lubricant coating film similarly to the solvent compositions in Examples 6 to 7, 13 to 14, and 20 to 21 in which a stabilizer is not included, in any cleaning test.

A solvent composition of the present invention is a stable solvent composition which is excellent in solubility of various organic substances and excellent in detergency and has a sufficient drying property, and has no adverse effect on a global environment, is excellent in stability, and moreover suppresses metal corrosion under coexistence with metal, and can be used for articles of various materials such as metal, plastic, elastomer, and fabric in a wide range of industrial uses such as a cleaning solvent, a dilution coating solvent, and a spraying agent composition without giving adverse effects.

What is claimed is:

1. A solvent composition comprising:
1-chloro-2,3,3-trifluoro-1-propene; and 1-chloro-2,2,3,3-tetrafluoropropane, wherein
a proportion of a content of 1-chloro-2,2,3,3-tetrafluoropropane to a total of a content of 1-chloro-2,3,3-trifluoro-1-propene and the content of 1-chloro-2,2,3,3-tetrafluoropropane is from 0.0001 to 1 mass %.

2. The solvent composition according to claim 1, wherein a proportion of an amount of 1-chloro-2,3,3-trifluoro-1-propene to a total amount of the solvent composition is 80 mass % or more.

3. The solvent composition according to claim 1, wherein the 1-chloro-2,3,3-trifluoro-1-propene consists of (Z)-1-chloro-2,3,3-trifluoro-1-propene and (E)-1-chloro-2,3,3-trifluoro-1-propene, and a proportion of an amount of (Z)-1-chloro-2,3,3-trifluoro-1-propene to a total amount of 1-chloro-2,3,3-trifluoro-1-propene is from 80 to 100 mass %.

4. A cleaning method comprising:
bringing the solvent composition according to claim 1 and an article to be cleaned into contact with each other.

5. The cleaning method according to claim 4, wherein a processing oil adheres to the article to be cleaned.

6. The cleaning method according to claim 5, wherein the processing oil is at least one selected from the group consisting of a cutting oil, a quenching oil, a rolling oil, a lubricating oil, a machine oil, a presswork oil, a stamping oil, a drawing oil, an assembly oil, and a wire drawing oil.

7. The cleaning method according to claim 4, wherein the article to be cleaned is clothing.

8. A method of forming a coating film comprising:
dissolving a nonvolatile organic compound in the solvent composition according to claim 1 to prepare a coating film-forming composition;
applying the coating film-forming composition on an article to be coated; and
evaporating the solvent composition after the applying of the coating film-forming composition to form a coating film consisting of the nonvolatile organic compound.

9. A heat transfer fluid comprising the solvent composition according to claim 1.

10. A heat cycle system comprising the heat transfer fluid according to claim 9.

11. The solvent composition according to claim 1, wherein the proportion of the content of 1-chloro-2,2,3,3-tetrafluoropropane to the total of the content of 1-chloro-2,3,3-trifluoro-1-propene and the content of 1-chloro-2,2,3,3-tetrafluoropropane is from 0.0005 to 0.1 mass %.

12. The solvent composition according to claim 1, wherein the proportion of the content of 1-chloro-2,2,3,3-tetrafluoropropane to the total of the content of 1-chloro-2,3,3-trifluoro-1-propene and the content of 1-chloro-2,2,3,3-tetrafluoropropane is from 0.01 to 0.05 mass %.

13. The solvent composition according to claim 2, wherein the proportion of the amount of 1-chloro-2,3,3-trifluoro-1-propene to the total amount of the solvent composition is 90 mass % or more.

14. The solvent composition according to claim 3, wherein the proportion of the amount of (Z)-1-chloro-2,3,3-trifluoro-1-propene to the total amount of 1-chloro-2,3,3-trifluoro-1-propene is from 90 to 100 mass %.

15. The solvent composition according to claim 3, wherein the proportion of the amount of (Z)-1-chloro-2,3,3-trifluoro-1-propene to the total amount of 1-chloro-2,3,3-trifluoro-1-propene is from 80 to 99.9 mass %.

16. The solvent composition according to claim 3, wherein the proportion of the amount of (Z)-1-chloro-2,3,3-trifluoro-1-propene to the total amount of 1-chloro-2,3,3-trifluoro-1-propene is from 90 to 99.9 mass %.

* * * * *